(12) United States Patent
Hess et al.

(10) Patent No.: US 7,251,532 B2
(45) Date of Patent: Jul. 31, 2007

(54) MEDICAL LEAD FIXATION

(75) Inventors: Douglas N. Hess, Maple Grove, MN (US); Nicolaas M. Lokhoff, Kerkrade (NL); Michael A. Ruff, Blaine, MN (US); Richard D. Sandstrom, Scandia, MN (US); Timothy G. Laske, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 398 days.

(21) Appl. No.: 10/688,229

(22) Filed: Oct. 17, 2003

(65) Prior Publication Data

US 2005/0085886 A1  Apr. 21, 2005

(51) Int. Cl.
*A61N 1/05* (2006.01)
(52) U.S. Cl. .................................................... 607/127
(58) Field of Classification Search ................. 606/60, 606/129; 623/72; 607/126, 127
See application file for complete search history.

(56) References Cited

U.S. PATENT DOCUMENTS

| 3,737,579 | A |   | 6/1973  | Bolduc ..................... 128/418 |
|-----------|---|---|---------|-------------------------------------|
| 3,754,555 | A |   | 8/1973  | Schmitt .................... 128/418 |
| 4,136,703 | A | * | 1/1979  | Wittkampf ................. 607/125 |
| 4,157,720 | A |   | 6/1979  | Greatbatch .............. 128/419 P |
| 4,357,946 | A |   | 11/1982 | Dutcher et al. ............. 128/785 |
| 4,463,765 | A | * | 8/1984  | Gold .......................... 607/127 |
| 4,497,326 | A |   | 2/1985  | Curry ........................ 128/785 |
| 5,246,014 | A |   | 9/1993  | Williams et al. ............ 607/122 |
| 5,255,693 | A |   | 10/1993 | Dutcher et al. ............. 607/120 |
| 5,259,394 | A |   | 11/1993 | Bens ........................... 607/127 |
| 5,609,621 | A | * | 3/1997  | Bonner ....................... 607/122 |
| 5,658,327 | A |   | 8/1997  | Altman et al. .............. 607/127 |
| 5,716,391 | A | * | 2/1998  | Grandjean ................... 607/127 |
| 5,964,795 | A | * | 10/1999 | McVenes et al. ........... 607/122 |
| 5,972,013 | A |   | 10/1999 | Schmidt ...................... 606/185 |
| 6,102,887 | A |   | 8/2000  | Altman ........................ 604/22 |
| 6,144,882 | A |   | 11/2000 | Sommer et al. ............ 607/125 |
| 6,256,541 | B1|   | 7/2001  | Heil et al. ................... 607/123 |
| 6,298,272 | B1| * | 10/2001 | Peterfeso et al. ........... 607/120 |
| 6,416,510 | B1| * | 7/2002  | Altman et al. ................ 606/41 |
| 6,478,776 | B1| * | 11/2002 | Rosenman et al. .... 604/164.01 |
| 6,556,874 | B2|   | 4/2003  | Audoglio ..................... 607/126 |
| 6,685,648 | B2|   | 2/2004  | Flaherty et al. ............. 600/464 |
| 6,937,897 | B2| * | 8/2005  | Min et al. ........................ 607/9 |
| 2001/0007070 | A1| * | 7/2001 | Stewart et al. ................ 606/41 |
| 2002/0138109 | A1| * | 9/2002 | Keogh et al. ................... 607/9 |
| 2004/0059404 | A1|   | 3/2004 | Bjorklund et al. .......... 607/126 |
| 2004/0102830 | A1|   | 5/2004 | Williams ..................... 607/125 |

FOREIGN PATENT DOCUMENTS

WO   WO 92/21405   10/1992

* cited by examiner

*Primary Examiner*—Scott A. Getzow
(74) *Attorney, Agent, or Firm*—Carol F. Barry; Girma Wolde-Michael

(57) ABSTRACT

A distal tip coupled to a body of an implantable medical device includes a canted passageway extending distally from a lumen of the body and an opening terminating the passageway and positioned in proximity to a distal end of the distal tip; a helical fixation element coupled to an elongated member extending within the lumen of the body is adapted to deflect along the canted passageway of the distal tip. The elongated member is adapted to move the helical member through the passageway of the distal tip and out from the opening and to rotate the helical element thereby affixing the helical element into an implant site.

22 Claims, 7 Drawing Sheets

MEDICAL LEAD FIXATION

TECHNICAL FIELD

The invention relates to medical devices and, more particularly, to configurations of distal of implantable medical leads facilitating fixation at an implant site.

BACKGROUND

In the medical field, implantable leads are used with a wide variety of medical devices. For example, implantable leads are commonly used to form part of implantable cardiac pacemakers that provide therapeutic stimulation to the heart by sensing electrical activity of the heart and delivering pacing, cardioversion or defibrillation pulses via electrodes disposed on the leads, e.g., typically near distal ends of the leads. Leads may also be used to deliver therapeutic agents. A number of challenges exist with respect to medical leads; in particular, as more advanced and complex therapeutic techniques are developed, new configurations are required to facilitate fixation of lead electrodes at alternate implant sites within a patient.

BRIEF DESCRIPTION OF THE DRAWINGS

The following drawings are illustrative of particular embodiments of the invention and therefore do not limit its scope, but are presented to assist in providing a proper understanding of the invention. The drawings are not to scale (unless so stated) and are intended for use in conjunction with the explanations in the following detailed description. The present invention will hereinafter be described in conjunction with the appended drawings, wherein like numerals denote like elements, and.

DETAILED DESCRIPTION

The following detailed description is exemplary in nature and is not intended to limit the scope, applicability, or configuration of the invention in any way. Rather, the following description provides a practical illustration for implementing exemplary embodiments of the invention.

Figure 1:
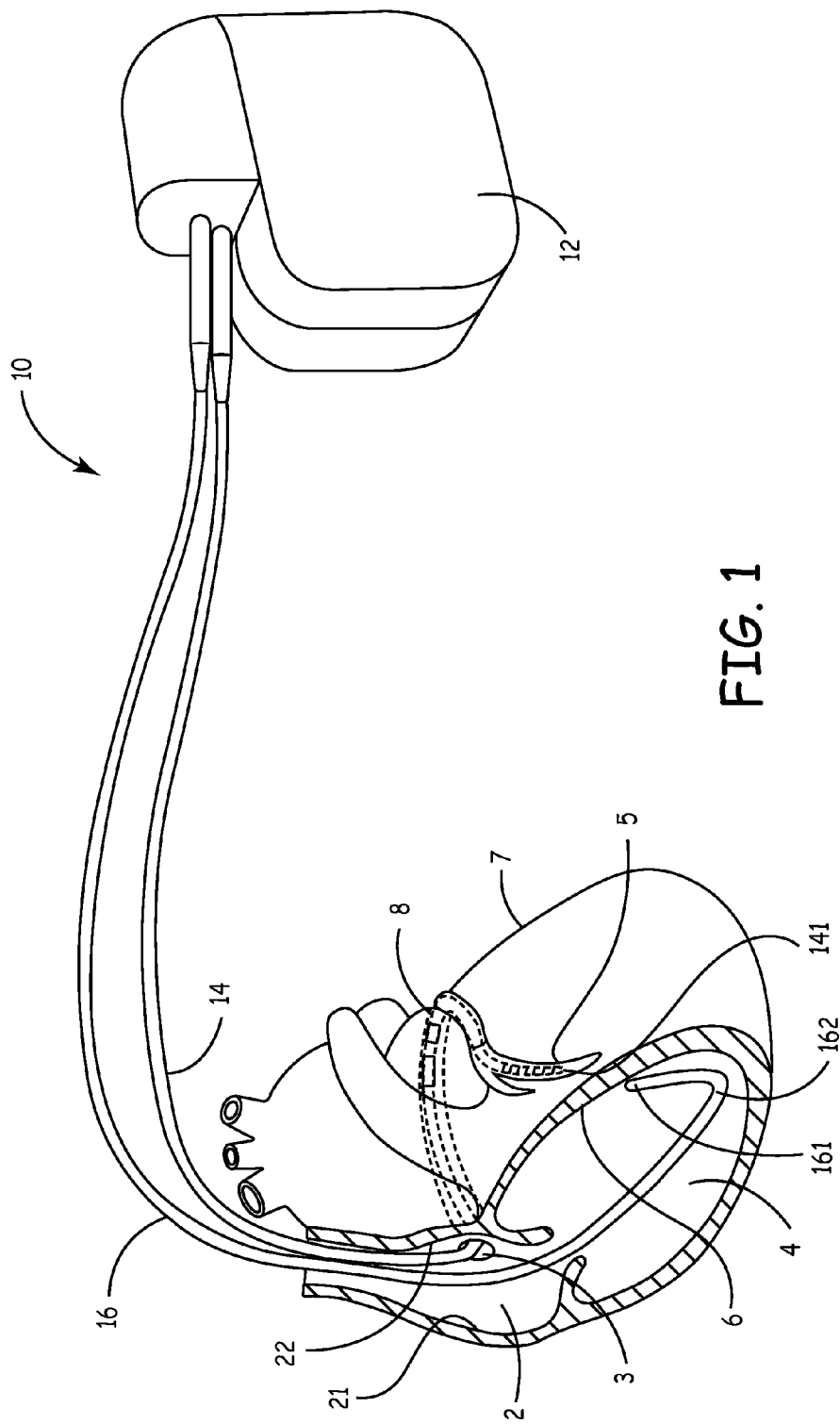
FIG. 1 is a conceptual overview of a system according to one embodiment of the present invention.

FIG. 1 is a conceptual overview of a system according to one embodiment of the present invention. FIG. 1 illustrates a system 10 including an implantable medical device (IMD) 12 and a first lead 14 and a second lead 16 electrically coupled to IMD 12, each lead including distal tips 141 and 161, respectively, configured to facilitate fixation at implant sites so that therapeutic stimulation pulses and/or agents can be delivered through leads 14, 16 to a heart from IMD 12. IMD 12 can deliver pacing, cardioversion and/or defibrillation therapy to a patient via electrodes disposed on leads 14, 16, however, embodiments of the present invention are not limited for use in therapy delivery and leads 14, 16 may include physiological sensors gathering data for patient monitoring devices or for devices that integrate monitoring and therapy delivery features. Such IMD's and devices along with connection means for associated leads are well known to those skilled in the art.

As illustrated in FIG. 1, lead 14 is implanted in a cardiac vein 8, fixed to a left ventricular epicardial site 5 of the heart, while lead 16 is implanted in a right ventricular chamber 4, fixed to a septal wall 6. According to embodiments of the present invention, distal tips 141 and 161 of leads 14 and 16 include a fixation element, which may extend therefrom at an angle to facilitate fixation at the illustrated implant sites; embodiments of such a configuration will be described in detail below. Implant sites made more viable by embodiments of the present invention also include those in a right atrial chamber 2, for example sites on a atrial lateral wall 21 and on an atrial septal wall 22, and epicardial sites accessed transthoracically, for example a left ventricular lateral site 7; furthermore, embodiments of the present invention are not limited to cardiac implantation and may also find use in other locations of a body, for example for neuro-stimulation or drug delivery.

Figure 2A:
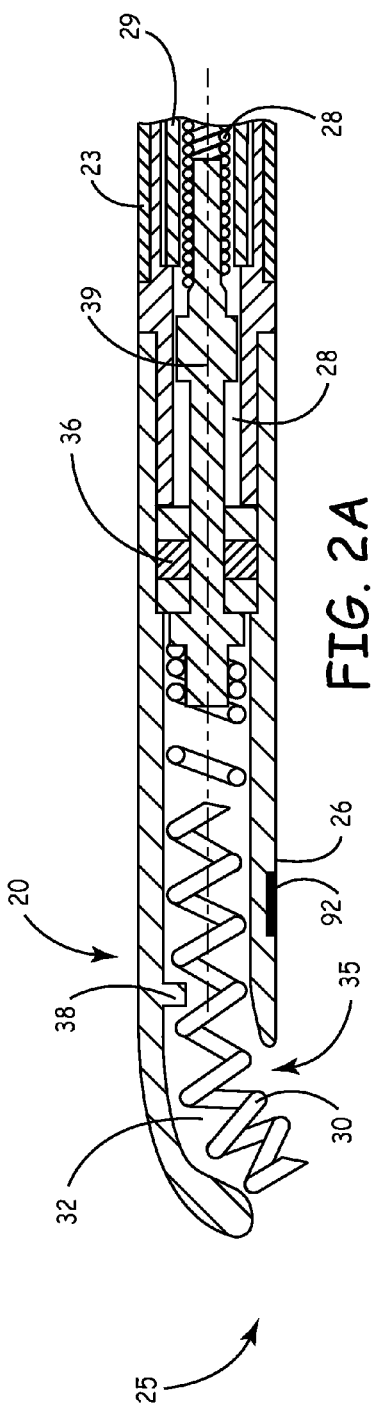
FIG. 2A is cross-sectional side view of a distal portion of a medical lead according to one embodiment of the present invention.

FIG. 2A is cross-sectional side view of a distal portion of a medical lead according to one embodiment of the present invention. FIG. 2A illustrates a lead distal tip 20 coupled to a distal end of a lead body 23 and including a canted passageway 32 and an opening 35 positioned in proximity to a distal tip distal end 25 and terminating passageway 32; passageway 32 extends distally from a lumen 28 of body 23 through which an elongated member 29 extends. Materials from which distal tip 20 may be formed include but are not limited to insulative polymers, one example of which is polyurethane. FIG. 2A further illustrates elongated member 29 coupled to a helical fixation element 30 via a stud component 39, which bridges lumen 28 and passageway 32 passing through a fluid tight seal 36; according the illustrated embodiment, elongated member 29 is formed as a coil and is adapted move helical element 30 through passageway 32 and out opening 35 and to rotate helical element 30, guided by a protrusion 38 formed within passageway 32, thereby affixing helical element 30 to an implant site (FIG. 1). Such a mechanism for moving a helical fixation element is well known to those skilled in the art and is typically activated at a proximal end of lead body 23 via a rotating connector pin coupled to a proximal end of elongated element 29.

According to embodiments of the present invention, helical element 30 is adapted to deflect by flexing along its length so that it may be moved along canted passageway 32 and out opening 35; materials forming helical element 30, which allow such flexing, comprise, but are not limited to, platinum, iridium, titanium, nickel, polycarbonate, and polypropylene. Appropriate materials may be selected by those skilled in the art depending upon functional requirements for helical element 30, for example, if helical element is only required for fixation, materials including synthetic resins and super-elastic metals, such as Nitinol, may be selected, while if helical element is further required to function as an electrode, a platinum-iridium alloy may be selected and coupled to elongated member 29, which also functions as a conductor, via a conductive stud component 39. According to additional embodiments, helical element 30 further provides a means for delivering a therapeutic agent, as will be further described in conjunction with FIG. 8. Referring back to FIG. 1, it can be seen that, according to the present invention, canted passageway 32 provides means to fix a lead to an implant site when that site is in a plane generally parallel with a longitudinal axis of the lead.

Referring back to FIG. 1, according to embodiments of the present invention, leads 14 and 16 further include pre-formed curvatures to facilitate orientation of distal tips 141, 161, for example a curvature 162 is pre-formed, according to methods known to those skilled in the art, in a distal portion of lead 16 such that distal tip 161 is positioned in proximity to an implant site along septal wall 6 with an opening in tip 161, similar to opening 35 (FIGS. 2A-B), facing toward septal wall 6. In another exemplary embodiment, lead 14 is formed with a curve in a manner corresponding to that described in commonly assigned U.S. Pat. No. 6,144,882, the relevant teachings of which are herein incorporated by reference, wherein the curve serves to hold lead 14 in coronary vein 8 such that an opening, e.g. opening 35, faces toward epicardial site 5.

Figure 2B:
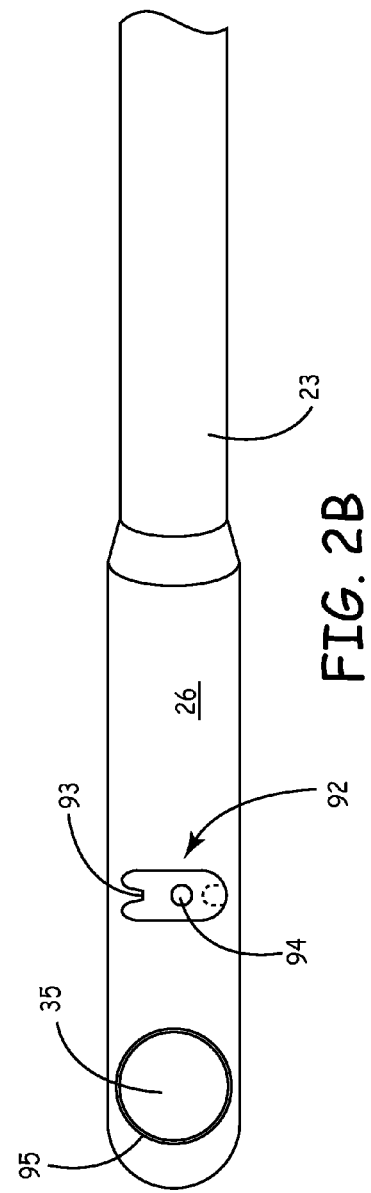
FIG. 2B is a plan view of the distal end of the lead shown in FIG. 2A according to one embodiment.

FIG. 2B is a plan view of the distal end of the lead shown in FIG. 2A according to one embodiment. FIG. 2B illustrates distal tip 20 including a radiopaque marker 92, which includes a first indicator 93 and a second indicator 94, configured to facilitate orientation of opening 35 toward an implant site by means of fluoroscopic visualization in a viewing plane coinciding with that of the implant site. First indicator 93 is an exemplary embodiment of an indicator designed to indicate whether opening 35 is generally directed toward implant site, when located in a top position, as illustrated in FIG. 2B, or generally directed away from implant site, when located in a bottom position, indicated by dashed lines, or visa versa depending on the direction of fluoroscopic viewing. Second indicator 94, according to one embodiment, provides a means for further orienting opening 35 in that a true circular form visualized indicates that opening is aligned with the viewing plane, while an ovular form indicates that opening 35 is skewed away from the viewing plane, and no view at all of second indicator 94 indicates that opening 35 is approximately perpendicular to viewing plane; an alternate embodiment of such an indicator includes a marker ring 95 formed about opening 35. Although marker 92 is illustrated attached to a base 26 of distal tip 20, in generally the same plane as opening 35, marker may be positioned elsewhere in distal tip 20.

Figure 3:
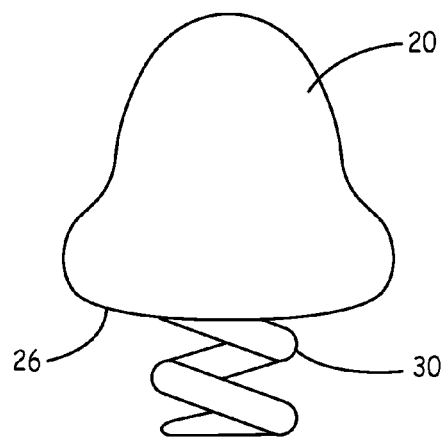
FIG. 3 is an end view of a distal tip of a lead according to an embodiment of the present invention.
Figure 4:
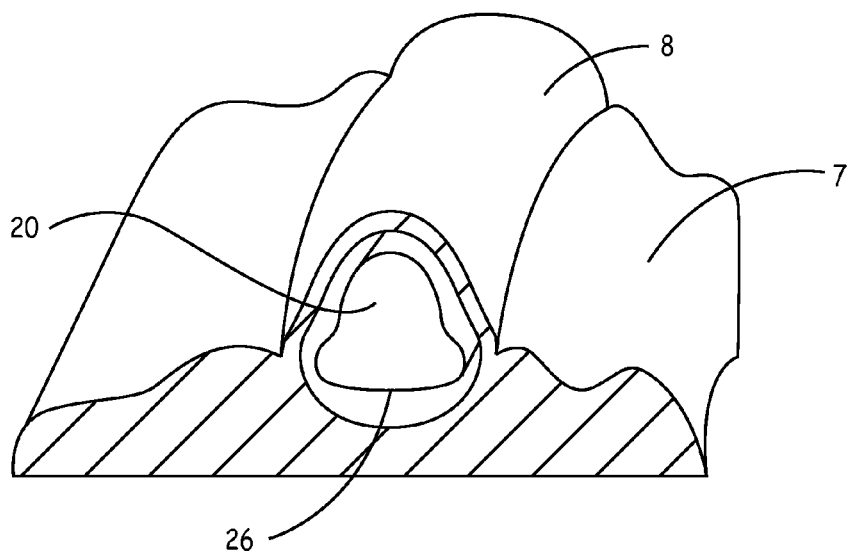
FIG. 4 is a conceptual perspective view of the distal tip, shown in FIG. 3, within a vein of a heart.

FIG. 3 is an end view of distal tip 20 according to an embodiment of the present invention; and FIG. 4 is a conceptual perspective view of distal tip 20 within vein 8 (FIG. 1). FIGS. 3 and 4 illustrate distal tip 20 including an asymmetrical radial section, which facilitates orientation of base 26 toward epicardial surface 7 so that helical fixation element 30 may be fixed at an implant site therein. The section illustrated in FIGS. 3 and 4 is generally bell-shaped according to one embodiment, however, any asymmetrical shaped radial section, which induces self-alignment of tip 20 within a coronary vein, i.e. vein 8, so that helical element 30 extends out from opening 35 (FIGS. 2A-B) toward epicardial surface 7, is within the scope of the present invention.

Figure 5A:
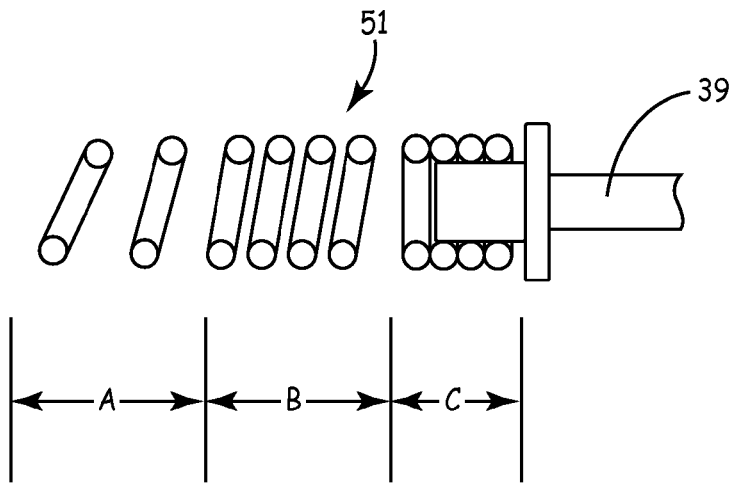
FIGS. 5A-B are section views of a helical fixation element according to embodiments of the present invention.
Figure 5B:
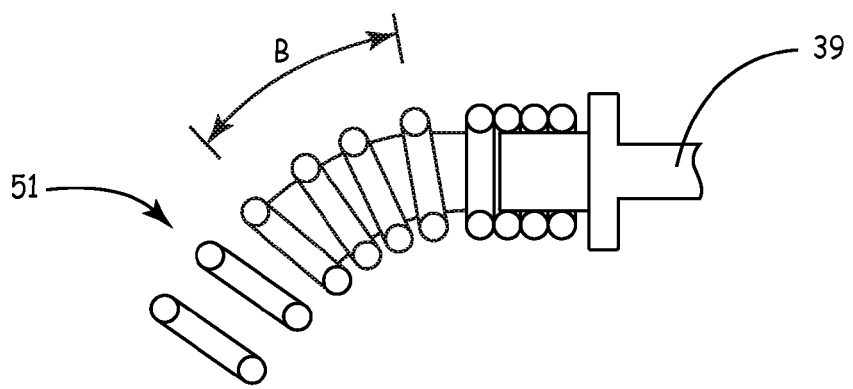

FIGS. 5A-B are section views of a helical fixation element according to alternate embodiments of the present invention. FIG. 5A illustrates a helical element 51 including a first pitch along length A, a second pitch along length B and a third pitch along length C; second and third pitches, along lengths B and C, respectively, may be substantially equivalent. The pitch refers to the lateral distance associated with one revolution of a helical element. According to one embodiment of the present invention, pitch along length A is optimized for rotation into tissue in order to affix a lead at an implant site, dimensions of which have be established and are known to those skilled in the art, while pitch along length B is smaller than that along length A in order to facilitate deflection through a canted passageway of a distal tip, for example passageway 32 of tip 20 illustrated in FIG. 2A. In particular, reduced helical pitch can cause helical element 51 to have reduced stiffness in area B relative to area A, making helical element 51 better suited for forced deflection. Area C defines a region for attachment to stud component 39, such as via a laser weld. FIG. 5B illustrates another embodiment in which helical element 51 includes a pre-formed deflection along length B which would be held straight within a straight portion of the canted passageway and then resume the pre-formed shape upon movement of length B into a curved portion of the canted passageway.

Figure 6:
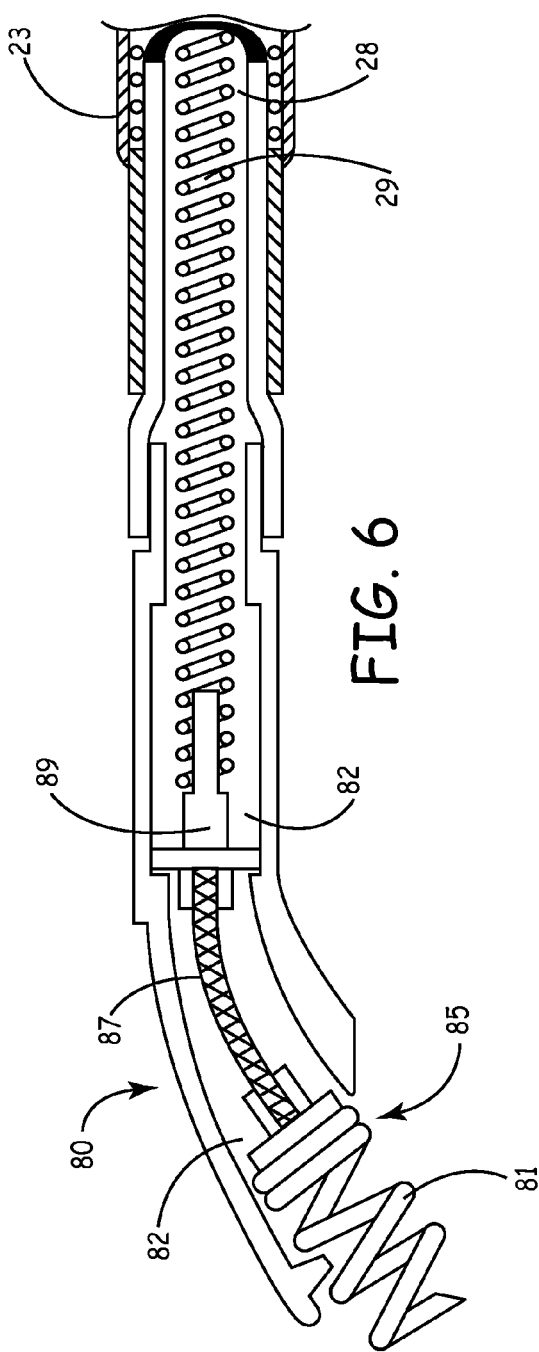
FIG. 6 is a cross-sectional side view of a distal portion of a medical lead according to an alternate embodiment of the present invention.

FIG. 6 is a cross-sectional side view of a distal portion of a medial lead according to an alternate embodiment of the present invention. FIG. 6 illustrates helical element 81 within a canted passageway 82 of a distal tip 80 and including a flexible coupling 87 positioned in between a stud component 89 attached to elongated element 29; according to this alternate embodiment, flexible coupling 87 facilitates movement of helical element 81, which may not bend along its length, through canted passageway 82. According to one embodiment, flexible coupling 87 comprises a cable, and in another embodiment a spring; and, if helical element 81 further functions as an electrode, flexible coupling 87 would comprise an electrically conductive material. In an alternate embodiment flexible coupling 87 comprises an elastic material and may be pre-formed to conform to the curvature of canted passageway 82, being held straight when retracted into a straight portion of passageway 82.

Figure 7:
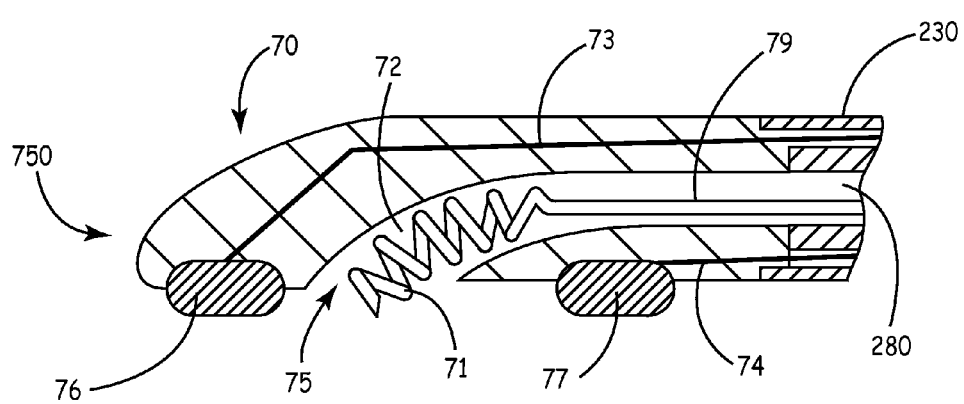
FIGS. 7 and 8 are cross-section side views of distal portions of leads according to additional alternate embodiments of the present invention.

FIG. 7 is a cross-section side view of a distal portion of a lead according to another embodiment of the present invention. FIG. 7 illustrates a distal tip 70 coupled to a distal end of a lead body 230 and including a canted passageway 72 extending from a lumen 280 of lead body 230 to an opening 75 in proximity to a distal end 750 of distal tip 70; a deflectable helical fixation element 71 is within canted passageway 72 and coupled to an elongated member 79, which extends proximally within lumen 280 of lead body 230 and serves to move helical element 71 through passageway 72 an out opening 75 for fixation at an implant site. FIG. 7 further illustrates distal tip 70 including a first electrode 76 positioned distal to opening 75 and a second electrode 77 positioned proximal to opening 75, each electrode coupled to a conductor, 73 and 74, respectively, which extend within lead body 230 to an electrical connector coupled to a proximal end of lead body 230. According to a first set of embodiments, helical element 71 does not function as an electrode; according to one of these embodiments, first and second electrodes 76, 77 function as a bipolar pair or as independent electrodes of the same polarity and, according to another of these embodiments, only first electrode 76 is included in tip 70 or only second electrode 77 is included in tip 70. According to a second set of embodiments helical element 71 also functions as an electrode; this set also includes alternate embodiments wherein either one or both of electrode 76, 77 are included for bipolar or unipolar function. It can be seen in FIG. 7 that the positions of electrodes 76 and 77 with respect to opening 75 facilitates good contact at an implant site in proximity to fixation by helical element 71.

Figure 8:
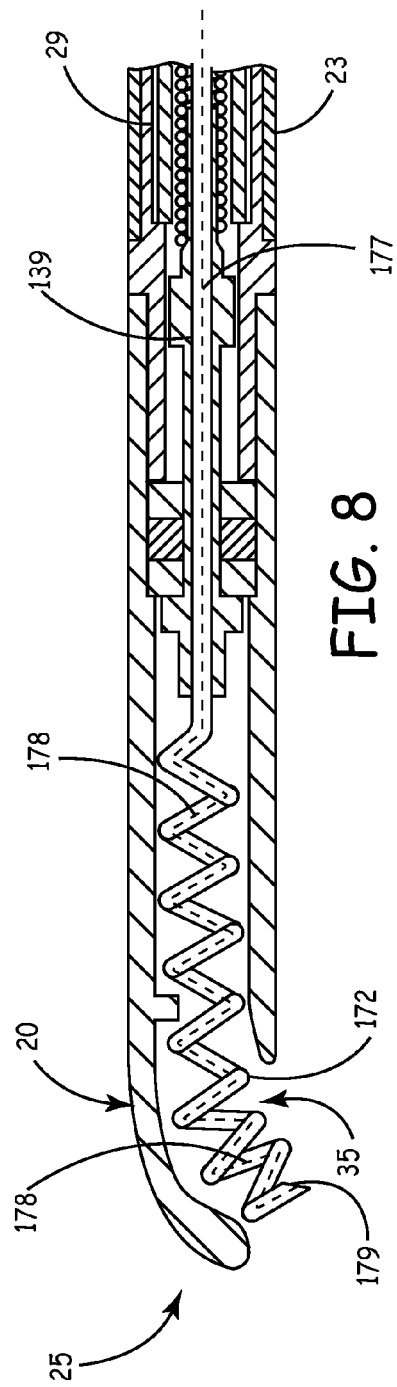

FIG. 8 is a cross-section side view of a distal portion of a lead according to yet another embodiment of the present invention. FIG. 8 illustrates distal tip 20 coupled to lead body 23, as in FIG. 2A, wherein elongated member 29 further includes a fluid delivery lumen 177 coupled to, or in fluid communication with a fluid infusion lumen 178 of a deflectable helical fixation element 172, which terminates in an exit port 179 at a distal end of element 172. A stud component 139 serves to couple helical element 172 to elongated element 29 and to generally align fluid lumens 177, 178; according to one embodiment, as illustrated in FIG. 8, helical element 172 is formed form a hypo-tube which is welded to a distal end of stud 139 and fluid delivery lumen 177 is formed by a tubing extending within elongated member 29 and through a bore of stud 139. Fluid lumens 177, 178 may used to deliver a contrast agent to help maneuver tip 20 to an implant site or to deliver therapeutic agents for treating tissue, into which helical member is fixed, at an implant site, or for both. Although not shown, it is apparent that fluid delivery lumen 177 extends to a proximal end of lead body 23 where it is coupled to a fluid delivery reservoir including a means for pumping the fluid through lumens 177, 178.

In the forgoing detailed description, the invention has been described with reference to specific embodiments. However, it may be appreciated that various modifications and changes can be made without departing from the scope of the invention as set forth in the appended claims.

The invention claimed is:

1. An implantable medical device, comprising
an elongated body including a lumen and an elongated member extending within the lumen;
a distal tip coupled to the body, the distal tip including a canted passageway extending distally from the lumen of the body, and an opening terminating the passageway; the opening positioned in proximity to a distal end of the distal tip, and the opening being oriented in a plane approximately parallel with a longitudinal axis of the distal tip; and
a helical fixation element coupled to the elongated member and adapted to deflect along the canted passageway of the distal tip;
wherein the elongated member is adapted to move the helical element through the passageway of the distal tip and out the opening, and to rotate the helical element thereby affixing the helical element into an implant site.

2. The medical device of claim 1, wherein the helical fixation element deflects by means of a flexible coupling with the elongated member.

3. The medical device of claim 2, wherein the flexible coupling comprises a cable.

4. The medical device of claim 2, wherein the flexible coupling comprises a spring.

5. The medical device of claim 2, wherein the flexible coupling is pre-formed to conform to a curvature of the canted passageway.

6. The medical device of claim 1, wherein the helical fixation element comprises a platinum-iridium alloy.

7. The medical device of claim 1, wherein the helical fixation element comprises a super-elastic metal.

8. The medical device of claim 1, wherein the helical fixation element comprises a synthetic resin.

9. The medical device of claim 1, wherein the elongated member comprises a conductor and the helical fixation element comprises an electrode.

10. The medical device of claim 1, wherein the body further includes an elongated conductor extending therein and the distal tip further includes an electrode coupled to the conductor.

11. The medical device of claim 10, wherein the electrode is positioned adjacent to and distal to the opening of the distal tip.

12. The medical device of claim 10, wherein the electrode is positioned adjacent to and proximal to the opening of the distal tip.

13. medical device of claim 1, wherein the distal tip further includes an asymmetrical radial section, the radial section being approximately perpendicular to the plane of the opening and facilitating orientation of the opening of the distal tip toward the implant site.

14. The medical device of claim 13, wherein the asymmetrical radial section is generally bell-shaped.

15. The medical device of claim 1, wherein the elongated body includes a curved distal portion in proximity to the coupling with the distal tip, the curved distal portion facilitating orientation of the opening of the distal tip toward the implant site.

16. An implantable medical device comprising:
an elongated body including a lumen and an elongated member extending within the lumen;
a distal tip coupled to the body, the distal tip including a canted passageway extending distally from the lumen of the body, and an opening terminating the passageway; the opening positioned in proximity to a distal end of the distal tip, and the opening being oriented in a place approximately parallel with a longitudinal axis of the distal tip; and
a helical fixation element coupled to the elongated member and adapted to deflect along the canted passageway of the distal tip;
wherein the elongated member is adapted to move the helical element through the passageway of the distal tip and out the opening and to rotate the helical element thereby affixing the helical element into an implant site,
wherein the helical fixation element deflects by flexing along its length.

17. The medical device of claim 16, wherein the helical fixation element includes a pitch change facilitating the deflection along its length.

18. An implantable medical device comprising:
an elongated body including a lumen and an elongated member extending within the lumen;
a distal tip coupled to the body, the distal tip including a canted passageway extending distally from the lumen of the body and an opening terminating the passageway; the opening positioned in proximity to a distal end of the distal tip, and being oriented in a plane approximately parallel with a longitudinal axis of the distal tip; and
a helical fixation element coupled to the elongated member and adapted to deflect along the canted passageway of the distal tip;
wherein the elongated member is adapted to move the helical element through the passageway of the distal tip and out the opening, and to rotate the helical element thereby affixing the helical element into an implant site,
wherein the helical fixation element is pre-formed along its length to conform to a curvature of the canted passageway.

19. An implantable medical device comprising:
an elongated body including a lumen and an elongated member extending within the lumen;

a distal tip coupled to the body, the distal tip including a canted passageway extending distally from the lumen of the body, and an opening terminating the passageway; the opening positioned in proximity to a distal end of the distal tip, and the opening being oriented in a plane approximately parallel with a longitudinal axis of the distal tip; and a helical fixation element coupled to the elongated member and adapted to deflect along the canted passageway of the distal tip;

wherein the elongated member is adapted to move the helical element through the passageway of the distal tip and out the opening and to rotate the helical element thereby affixing the helical element into an implant site, wherein the distal tip further includes a radiopaque marker facilitating orientation of the opening of the distal tip toward the implant site via fluoroscopic visualization.

20. The medical device of claim 19, wherein the marker includes an indicator indicating whether the opening of the tip is directed generally toward or away from a plane coinciding with that of the implant site.

21. The medical device of claim 19, wherein the marker includes an indicator indicating a degree to which the opening is angled with respect to a plane coinciding with that of the implant site.

22. An implantable medical device comprising:

an elongated body including a lumen and an elongated member extending within the lumen;

a distal tip coupled to the body, the distal tip including a canted passageway extending distally from the lumen of the body, and an opening terminating the passageway; the opening positioned in proximity to a distal end of the distal tip, and the opening being oriented in a plane approximately parallel with a longitudinal axis of the distal tip; and a helical fixation element coupled to the elongated member and adapted to deflect along the canted passageway of the distal tip;

wherein the elongated member is adapted to move the helical element through the passageway of the distal tip and out the opening and to rotate the helical element thereby affixing the helical element into an implant site, wherein the elongated member includes a fluid delivery lumen and the helical fixation member includes a fluid infusion lumen in fluid communication with the fluid delivery lumen in order that a desired fluid may be infused out from the opening of the distal tip.

* * * * *